United States Patent [19]
Jeannin et al.

[11] Patent Number: 6,162,820
[45] Date of Patent: Dec. 19, 2000

[54] METHOD FOR REMOVING PARASITES AND IN PARTICULAR ECTOPARASITES OF VERTEBRATES, IN PARTICULAR OF MAMMALS, AND COMPOSITIONS FOR THE IMPLEMENTATION OF THIS METHOD

[75] Inventors: Philippe Jeannin, Tournefeuille; Marc Teichner, Ste Foy les Lyons, both of France; Philid Reid Timmons, Durham; Kenneth Anthony Kukorowski, Raleigh, both of N.C.; Bruno Julia, Toulouse; Jean-Yves Vienot, Lyons, both of France; Tai-Teh Wu, Chapell Hill, N.C.

[73] Assignee: Merial, Lyons, France

[21] Appl. No.: 08/891,047

[22] Filed: Jul. 10, 1997

[30] Foreign Application Priority Data

Jul. 11, 1996 [FR] France ................................ 96 08703
Mar. 13, 1997 [FR] France ................................ 97 03025

[51] Int. Cl.$^7$ ................................................ A61K 31/415

[52] U.S. Cl. ........................ 514/407; 514/94; 987/84

[58] Field of Search ..................... 514/407, 94; 987/84

[56] References Cited

U.S. PATENT DOCUMENTS

| | | | |
|---|---|---|---|
| 4,963,575 | 10/1990 | Buntain et al. ............... | 514/359 |
| 4,981,085 | 1/1991 | D'Silva et al. ............... | 514/407 |
| 5,232,940 | 8/1993 | Hatton et al. ............... | 514/407 |
| 5,929,118 | 7/1999 | Kraatz et al. ............... | 514/599 |

OTHER PUBLICATIONS

USPATFUL abstract AN 90:30059, D'Silva et al, US patent 4,918,085, Apr. 17, 1990.

*Primary Examiner*—Keith D. MacMillan
*Attorney, Agent, or Firm*—Frommer Lawrence & Haug LLP; Thomas J. Kowalski; William S. Frommer

[57] ABSTRACT

Methods for removing parasites and in particular ectoparasites of vertebrates, in particular of mammals, and compositions for the implementation of this method.

Methods for removing parasites of vertebrates, and in particular arthropods, mainly insects and Arachnida, wherein an effectively parasiticidal amount of a compound of formula (I)

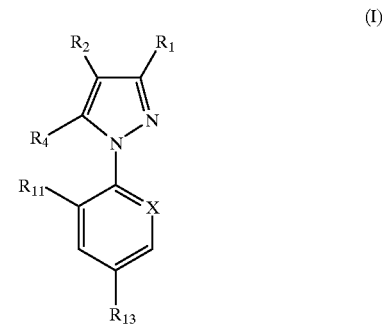

in particular of fipronil, is administered to the animal via an administration route which makes possible systemic distribution and good absorption.

23 Claims, No Drawings

METHOD FOR REMOVING PARASITES AND IN PARTICULAR ECTOPARASITES OF VERTEBRATES, IN PARTICULAR OF MAMMALS, AND COMPOSITIONS FOR THE IMPLEMENTATION OF THIS METHOD

The present invention relates to methods for removing parasites of vertebrates and in particular ectoparasites. Depending on the host-parasite pairs, a method according to the invention can take on a therapeutic aspect, when it is intended to prevent or treat parasitoses which are pathogenic in their nature or their induced effects, or a method may be without any therapeutic purpose, when the treatment consists in combatting parasites which cause non-pathological effects in their hosts, such as signs of discomfort or an unsightly appearance.

The invention also relates to compositions which make possible the implementation of these methods.

Parasite, within the meaning of the present invention, is understood to mean not only true parasites but also insects or other vermin capable of soiling occasional or permanent hosts or of otherwise harming them. The parasites targeted by the invention are mainly composed of arthropods and in particular insects and Arachnida, including Acarina.

More specifically, the invention relates in particular to the removal of fleas, in particular Ctenocephalides spp., in particular felis, ticks, in particular Rhipicephalus spp., in particular sanguineus, and Boophilus spp., in particular microplus, myiasis-causing parasites or mange, in particular Sarcoptes spp., in particular cabiei, and lice, in particular Damalinia spp. and Linognathus spp., in companion animals (in particular dogs and cats), cattle, goats and sheep, and Suidae.

It is already known to protect vertebrates against various parasites, and in particular arthropods, with 1-phenyl-3-cyanopyrazole derivatives, as described in Patent Applications WO 87/03781, 93/06089 and 94/21606 and European Patent Application EP-A-0,295,117. A number of methods which make possible an external application of compositions containing such compounds have been listed in these applications, in order to combat ectoparasites. These applications also generally list methods for oral or parenteral administration, without indicating the specific host/parasite pairs which would call for them.

The present invention proposes to provide new methods for combatting parasites which makes it possible to remove many ectoparasites of vertebrates, in particular of mammals.

A particularly noteworthy object of the invention is to provide methods which, by a single administration, make it possible to remove ectoparasites with an extremely high effectiveness for a long period of time.

The subject of the invention is methods for removing parasites of vertebrates and in particular, but not necessarily exclusively, ectoparasites of vertebrates and particularly of mammals and in particular arthropods, mainly insects and Arachnida, wherein an effectively parasiticidal amount of a compound of formula (I)

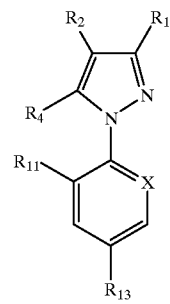

in which:

$R_1$ is a halogen atom, CN or methyl;

$R_2$ is $S(O)_n R_3$ or haloalkyl;

$R_3$ is alkyl or haloalkyl;

$R_4$ represents a hydrogen or halogen atom; or an $NR_5 SR_6$, $S(O)_m R_7$, $C(O)R_7$ or $C(O)OR_7$, alkyl, haloalkyl or $OR_8$ radical or an $N=C(R_9)(R_{10})$ radical;

$R_5$ and $R_6$ independently represent the hydrogen atom or an alkyl, haloalkyl, alkoxycarbonyl, C(O)alkyl or $S(O)_r CF_3$ radical; or $R_5$ and $R_6$ can together form a divalent alkylene radical which can be interrupted by one or two divalent heteroatoms, such as oxygen or sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted by one or more halogen atoms or groups such as OH, —O-alkyl, —S-alkyl, cyano or alkyl;

$R_{11}$ and $R_{12}$ represent, independently of one another, a hydrogen or halogen atom and optionally CN or $NO_2$ but H or halogen being preferred;

$R_{13}$ represents a halogen atom or a haloalkyl, haloalkoxy, $S(O)_q CF_3$ or $SF_5$ group;

m, n, q and r represent, independently of one another, an integer equal to 0, 1 or 2;

X represents a trivalent nitrogen atom or a $C$—$R_{12}$ radical, the three other valencies of the carbon atom forming part of the aromatic ring;

with the proviso that, when $R_1$ is methyl, then $R_3$ is haloalkyl, $R_4$ is $NH_2$, $R_{11}$ is Cl, $R_{13}$ is $CF_3$ and X is N, is administered to the animal via an administration route which makes possible systemic distribution and good absorption.

The alkyl radicals of the definition of the formula (I) generally comprise from 1 to 6 carbon atoms. The ring formed by the divalent alkylene radical representing $R_5$ and $R_6$ and the nitrogen atom to which $R_5$ and $R_6$ are attached is generally a 5-, 6- or 7-membered ring.

$R_5$ and $R_6$ can in particular independently represent the hydrogen atom or an alkyl, haloalkyl, C(O)alkyl or $S(O)_r CF_3$ radical; or $R_5$ and $R_6$ can together form a divalent alkylene radical which can be interrupted by one or two divalent heteroatoms, such as oxygen or sulphur.

A preferred class of compounds of formula (I) comprises the compounds such that $R_1$ is CN and/or $R_3$ is haloalkyl and/or $R_4$ is $NH_2$ and/or $R_{11}$ and $R_{12}$ are, independently of one another, a halogen atom and/or $R_{13}$ is haloalkyl, preferably $CF_3$.

Preference is also given to the compounds in which $R_2$ is $S(O)_nR_3$, preferentially with n=1, $R_3$ preferably being $CF_3$ or alkyl, for example methyl or ethyl, or alternatively n=0, $R_3$ preferably being $CF_3$.

A compound of formula (I) which is very particularly preferred in the invention is 1-[2,6-$Cl_2$-4-$CF_3$phenyl]-3-CN-4-[SO—$CF_3$]-5-$NH_2$pyrazole, hereinafter known as compound A and the common name of which is fipronil.

Another advantageous compound, in particular for oral administration, is 1-[2,6-$Cl_2$-4-$CF_3$phenyl]-3-CN-4-[S—$CF_3$]-5-NHLpyrazole. Another advantageous compound, for example, is 1-[2,6-$Cl_2$-4-$CF_3$phenyl]-3-CN-4-[S—$C_2H_5$]-5-NHLpyrazole.

Compounds of formula (I) can be prepared according to one or other of the methods described in Patent Applications WO 87/3781, 93/6089 and 94/21606 or European Patent Application 295,117 or any other method coming within the competence of the person skilled in the art who is a specialist in chemical synthesis. For the chemical preparation of the products of the invention, the person skilled in the art is regarded as having available, inter alia, all the contents of "Chemical Abstracts" and of the documents which are cited therein.

Effectively parasiticidal amount is understood to mean an amount which results in blood and/or tissue concentrations which are toxic by ingestion by parasitic arthropods, in particular biting, sucking or gnawing arthropods.

In an improvement of the invention, it is possible to administer one or more other relevant parasiticides, concomitantly or simultaneously and preferably in the form of a single preparation. Such another parasiticide will preferably be an endectocidal parasiticide of macrocyclic lactone type.

This associated parasiticide is preferably selected from the group formed by avermectins, ivermectin, abamectin, doramectin, moxidectin, milbemycins and the derivatives of these compounds.

According to a preferred embodiment of the invention, the administration of the effective dose to the animal is carried out once or a very small number of times for a duration of activity of at least one month and which can advantageously be two or three months or even six months. In other words, a permanent combatting method in an environment in which the animal is subjected to strong parasitic pressure, wherein a systemic administration is carried out at a frequency well below a daily administration, such as, for example, a monthly administration, or even less than a monthly frequency, for example quarterly or half-yearly.

Moreover, it is particularly noteworthy and surprising to be able to act effectively and for such long periods of time against ectoparasites which live in the integuments or on the fur of the animal by the administration of relatively low and non-toxic doses by systemic administration, without requiring the employment of controlled and long-lasting release means. The explanation for this phenomenon is not, for the moment, fully understood but seems related to the combination of a very long persistence of the compound with an exceptional toxicity by ingestion by the parasite.

The effective dose administered in the method according to the invention is preferably between 0.001, preferentially 0.01, and 100 mg/kg and, in a particularly preferred way, from 1 to 50 mg/kg of animal weight, the highest doses being provided for a very sustained release in the body of the animal.

Preferably, for the majority of host species, the dose and the composition are chosen so as to maintain a serum level of compound according to the formula (I) of greater than or equal to 1 ng/ml, for example 1 to 50 ng/ml.

The methods according to the invention are particularly effective in combatting fleas and ticks of small companion animals, in particular dogs. Serum levels of 20 to 30 ng/ml will be preferred against fleas and of 30 to 50 ng/ml against ticks.

The methods are also particularly effective against ticks, flies and myiasis-causing parasites which parasitize large animals and in particular cattle, goats and sheep.

The methods have also proved to be particularly effective in the treatment of porcine mange.

The dose can be administered in particular by the oral or parenteral route or by a topical formulation with a transcutaneous effect.

A particular subject of the invention is therapeutic methods according to the invention, intended for the treatment or prevention of parasitoses having pathogenic consequences, wherein, for example, they are applied in the elimination of myiasis-causing parasites, in particular in cattle, horses, goats or sheep, in regions where a significant pressure from these myiasis-causing parasites exists, or in the elimination of ticks, in particular in cattle, or optionally dogs, in regions where the pressure from ticks is of such a nature as to result in pathogenic consequences on a significant scale.

Another subject of the invention is methods with a non-therapeutic purpose, in particular for cleaning the coats of animals, and in particular dogs and companion animals, which are thus rid of parasites, in particular fleas, and their waste and excreta. The treated animal exhibits a coat which is pleasing to the eye and pleasant to the touch.

Other non-therapeutic methods according to the invention are applied, for example, in combatting harmful flies, in companion animals or income-producing animals, in particular raised under intensive conditions or in herds.

Another subject of the invention is compositions for the implementation of methods with a therapeutic purpose according to the invention.

Another subject of the invention is compositions for the implementation of non-therapeutic methods according to the invention, in particular for cleaning coats.

The compositions according to the invention are preferably provided for administration in a single dose or a dose repeated a small number of times and preferably comprise a dose of compound of formula (I) of between 0.01 and 100 mg/kg and preferably 1 to 50 mg/kg of body weight of the animal.

The compositions are effective over a fairly wide range of doses, which makes it possible to provide the same dosages for small animals having relatively different sizes.

For administration by the oral route, the composition can optionally be prepared at the time of use, for example by simple mixing of a powdered, or preferably dissolved, preparation of a compound of formula (I) into the food of the animal and in particular food prepared for dogs or cats. Use will preferably be made of the derivative of formula II.

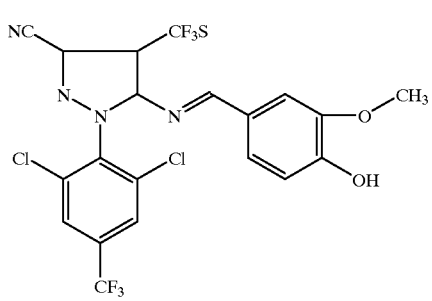

(II)

The composition can, however, also be provided in any other form suitable for oral administration, such as, for example, solutions or suspensions to be taken orally, emulsions, microemulsions, creams, pellets, tablets, gelatin capsules or others.

It is preferable for the excipient which forms part of the composition for oral administration to allow release in the intestines, and gastroprotected gelatin capsules or gastroresistant tablets are particularly preferred.

For large animals, preference is given to formulations in the form of powders, of rumen-resistant formulations, boli or intraruminal devices.

For administration by the parenteral route, preferably the subcutaneous or intramuscular route, the compound of formula (I) can be contained in a liquid excipient which is biologically suitable for injection in the solution, suspension, emulsion or microemulsion form.

The parenteral composition can also be produced in the particulate form, in particular nanoparticles and nanocapsules, microparticles, microcapsules or liposomes, or alternatively in the form of an implant.

The composition according to the invention can be presented in the form of a single dose without controlled release means. In this case, the dose is preferably between 1 and 20 mg/kg of body weight, which makes possible a long-lasting activity of several weeks to several months, which is altogether remarkable.

The compound of formula (I) can also be contained in a material which provides for controlled release. For example, the compound according to the invention can be contained in microspheres, granules or implants which make possible release by diffusion and/or erosion.

A releasable composition with a dose of between 1 and 50 mg/kg, preferably of 10 to 30 mg/kg, for example 20 mg/kg of body weight, consequently makes possible a long-lasting activity for several months, indeed a year.

Such controlled-release formulations are particularly suitable for administration by the parenteral route, for example by injection. They are particularly suitable for the case of cats or other animals with a rapid metabolization.

For transcutaneous-passage formulations, the composition can comprise the abovementioned particulate or liposomal forms, preferably in combination with an absorption promoter.

In an improvement of the invention, the composition according to the invention can also comprise at least one other relevant parasiticide. This parasiticide will preferably be an endectocidal parasiticide of macrocyclic lactone type.

This parasiticide is preferably selected from the group formed by avermectins, ivermectin, abamectin, doramectin, moxidectin, milbemycins and the derivatives of these compounds.

The effective amount of the endectocide in a dose is preferably between 0.1 mg/kg, preferentially 1 mg/kg, and 1 mg/kg, and, in a particularly preferred way, from 1 to 200 mg/kg of animal weight.

The proportions by weight of parasiticide of formula (I) to the associated parasiticide are preferably between 5/1 and 20,000/1.

It can be particularly advantageous for the parasiticide of formula (I) and the associated endectocidal parasiticide to be contained in a controlled- and sustained-release preparation, such as, for example, microspheres, granules or implants. This can be obtained, preferably, by mixing a controlled-release preparation of product, such as fipronil, and a controlled-release preparation of endectocide, preferably ivermectin, in a suitable vehicle, such as water, oil or a medium-chain triglyceride.

In such controlled-release preparations, the formulations are preferably drawn up so as to release between 5 and 100 mg/kg/day, for example 45 mg/kg/day, of compound of formula (I), for example fipronil, and from 0.01 to 15 mg/kg/day, for example 0.5 mg/kg/day, of endectocide, in particular ivermectin.

In the case of such controlled-release preparations, a dose for a treatment of very long duration of an animal will preferably comprise between 1 and 20 mg/kg of fipronil or other product of formula (I) and between 2 mg/kg and 3 mg/kg of endectocide, in particular of ivermectin.

Another subject of the invention is the use of the abovementioned compound corresponding to the formula (I) for the preparation of the compositions capable of being employed in the methods according to the invention. Among the compounds which it is preferable to use for this end is 1-[2,6-$Cl_2$-4-$CF_3$phenyl]-3-CN-4-[SO—$CF_3$]-5-$NH_2$pyrazole (fipronil).

Other advantages and characteristics of the invention will become apparent on reading the following description, given by way of non-limiting example.

EXAMPLE 1

Sixteen pigs, with an average weight of 21 kg, naturally infested with sarcoptic mange (Sarcoptes scabiei, variety suis), were randomly divided into 4 groups of 4 pigs each (1 untreated control group, 3 treatment groups).

The fipronil-based treatment was mixed with the food and administered once on day 0 at doses of 1.5, 6.25 and 25 mg/kg to the 3 treatment groups.

All the pigs were heavily infested by the agent of sarcoptic mange (scraping until blood emerges, then microscopic examination) and showed visible clinical signs of this infestation, of the blotches of the skin, pruritus and papules type.

Clinical and parasitological examinations carried out each week after treatment for 1 month showed 100% effectiveness in the treated groups whereas the sarcoptic mange persists in the untreated animals.

EXAMPLE 2

Twenty dogs of various breeds were randomly assigned to 4 groups of five animals each. A first group was used as untreated control. In the 3 other groups, each dog was treated once at D0 by the oral route with fipronil in the gelatin-capsule form at doses of 1, 10 and 20 mg/kg respectively in each group.

These animals were experimentally infested with 100 fleas (Ctenocephalides felis) and 50 ticks (Rhipicephalus sanguineus) at D1, D7 and weekly thereafter until 42 days after treatment.

Fleas and ticks were counted 2 days after each experimental infestation in order to evaluate the insecticidal activity in the treated groups.

A dose-duration of activity response was clearly demonstrated, i.e.:

At the dose of 1 mg/kg, 100% flea control was obtained for 2 weeks and 100% tick control was obtained for 1 week.

At the dose of 10 mg/kg, 100% flea control was obtained for 3 weeks and 100% tick control was obtained for 1 week.

At the dose of 20 mg/kg, 100% flea control was obtained for 5 weeks and 100% tick control was obtained for 2 weeks.

In addition to the dose-effect response demonstrated, this method made it possible to reveal that the systemic activity of fipronil by the oral route was superior in duration against the flea in comparison with the tick.

EXAMPLE 3

A group of 3 dogs weighing 10 kg is treated with a 3.3% m/V solution of fipronil in a mixture of organic solvents and of vegetable oil by the subcutaneous route at the rate of 0.3 ml/kg.

Minimum effective plasma concentrations are obtained for a duration of at least 3 months (fleas and ticks).

EXAMPLE 4

Four groups of 3 dogs weighing 10 kg are treated with microspheres made of poly(lactic acid) or poly(lactic-glycolic acid) polymer which make possible controlled release of fipronil. The polymer which confines the fipronil can be in particular PLA 100 D.L with a molecular weight of 100,000, PLA 100 D.L. with a weight of 26,000, PLGA 75/25 with a weight of 19,000 or PLGA 75/25 with a weight of 120,000, approximately, at 15% m/V in water or in a vegetable oil or in a medium-chain triglyceride (i.e. 3.3% m/V of fipronil) by the subcutaneous route at the rate of 0.3 ml/kg.

The fipronil dose administered is thus approximately 9 mg/kg.

Depending on the formulations injected, minimum effective plasma concentrations are obtained for durations of at least 2 months to 6 to 7 months (fleas and ticks).

EXAMPLE 5

A preparation of microspheres containing fipronil is prepared according to Example 4.

Microspheres containing ivermectin are prepared separately. Such microspheres can be prepared in a way known per se, for example as described in Application WO 95/13799. These microspheres are preferably contained in the same liquid vehicle as the microspheres containing fipronil, namely water, a vegetable oil or a medium-chain triglyceride.

The two preparations are mixed in proportions such that the injectable dose contains 9 mg of fipronil and 200 mg of ivermectin/kg and the dose is administered to 4 groups of 3 dogs.

What is claimed is:

1. A composition for oral administration comprising:

(i) an ectoparasiticidally effective amount of compound of formula (I)

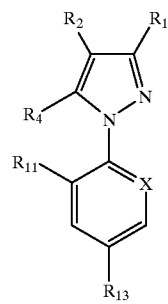

in which:

$R_1$ is a halogen atom, CN or methyl;

$R_2$ is $S(O)_n R_3$ or haloalkyl;

$R_3$ is alkyl or haloalkyl;

$R_4$ represents a hydrogen or halogen atom; or an $NR_5R_6$, $S(O)_m R_7$, $C(O)R_7$, or $C(O)OR_7$, alkyl, haloalkyl or $OR_8$ radical or a $-N=(R_9)(R_{10})$ radical;

$R_5$ and $R_6$ independently represent a hydrogen atom or an alkyl, haloalkyl, alkoxycarbonyl, C(O)alkyl, or $S(O)_r CF_3$, radical; or $R_5$ and $R_6$ may together form a divalent alkylene radical which may be interrupted by one or two divalent heteroatoms such as oxygen or sulfur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or groups such as OH, —O-alkyl, —S-alkyl, cyano or alkyl;

$R_{11}$ represents a hydrogen or halogen atom and optionally CN or $NO_2$;

$R_{13}$ represents a halogen atom or a haloalkyl, haloalkoxy, $S(O)_q CF_3$, or $SF_5$ group;

m, n, p and r represent, independently of each other, an integer equal to 0, 1 or 2;

X represents a trivalent nitrogen atom or a $C-R_{12}$ radical, the other three valencies of the carbon atom forming part of the aromatic ring;

with the proviso that when $R_1$ is methyl, then either $R_3$ is haloalkyl, $R_4$ is $NH_2$, $R_{11}$ is Cl, $R_{13}$ is $CF_3$ and X is N; and, (ii) a gastroprotective excipient; whereby, when the composition is ingested, the compound of formula (I) is released in the intestines.

2. The composition according to claim 1 wherein the gastroprotective excipient is a gastroprotected gelatin capsule.

3. The composition according to claim 1 wherein the gastroprotective excipient is a gastroresistant tablet.

4. The composition according to claim 1 wherein the gastroprotective excipient is gastroresistant gelatin.

5. The composition according to claim 1 wherein the gastroprotective excipient is a gastroresistant coating.

6. The composition according to claim 1 wherein the gastroprotective excipient is a gastroresistant carrier.

7. The composition according to claim 1 wherein the compound of formula (I) is 1-[2,6-Cl$_2$-4-CF$_3$phenyl]-3-CN-4-[SO—CF$_3$]-5NH$_2$pyrazole.

8. The composition according to claim 1 wherein the compound of formula (I) is in a dose of between 0.001 and 100 mg/kg of body weight of the animal.

9. The composition according to claim 8 wherein the dose is between 10 and 30 mg/kg of body weight of the animal.

10. The composition of claim 1, further comprising a macrocyclic lactone endectocidal parasiticide present in an endectoparasiticidally effective amount.

11. The composition according to claim 10 wherein the endectocidal parasiticide is an avermectin.

12. The composition according to claim 10 wherein the endectocidal parasiticide is selected from the group consisting of ivermectin, abamectin, doramectin, moxidectin, milbemycins and derivatives of these compounds.

13. The composition according to claim 12 wherein the endectocidal parasiticide is selected from the group consisting of ivermectin and abamectin.

14. The composition according to claim 13 wherein the endectocidal parasiticide comprises ivermectin.

15. The composition according to claim 13 wherein the endectocidal parasiticide comprises abamectin.

16. A method for the treatment or the prevention of a parasitic infection in a vertebrate animal which comprises orally administering a parasiticidally effective amount of the composition of any one of claims 1 to 15.

17. The method according to claim 16 wherein the animal is a cat or dog and the parasite is a flea or tick.

18. The method according to claim 16 wherein the parasiticidally effective amount comprises the compound of formula (I) in a dose of between 0.001 and 100 mg/kg of body weight of the animal.

19. The method according to claim 18 wherein the dose is between 10 and 30 mg/kg of body weight of the animal.

20. The method according to claim 16 wherein the composition is administered to the animal once a month.

21. The method according to claim 16 wherein the composition is administered to the animal once every two months.

22. The method according to claim 16 wherein the composition is administered to the animal once every three months.

23. The method according to claim 16 wherein the composition is administered to the animal once every six months.

* * * * *

UNITED STATES PATENT AND TRADEMARK OFFICE
CERTIFICATE OF CORRECTION

PATENT NO. : 6,162,820

DATED : Dec. 19, 2000

INVENTOR(s) : Philippe Jeannin et al.

It is certified that error appears in the above-identified patent and that said Letters Patent is hereby corrected as shown below:

On the cover page of the patent at line item [75] (Inventors:) change the third inventor's name from "Philid Reid Timmons" to –Philip Reid Timmons--.

On the cover page of the patent at line item [73] (Assignee:) change "Lyons" to --Lyon--.

Signed and Sealed this

Twenty-fourth Day of April, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,162,820
DATED : December 19, 2000
INVENTOR(S) : Jeannin et al.

Page 1 of 1

It is certified that error appears in the above-identified patent and that said Letters Patent is hereby corrected as shown below:

Claim 1,
Line 22 (column 8, line 22), change "-N=($R_9$)($R_{10}$) radical" to -- -N=C($R_9$)($R_{10}$) --; and
Line 38 (column 8, line 38), change "$SF_3$" to -- $SF_5$ --.

Signed and Sealed this

Twenty-third Day of October, 2001

Attest:

NICHOLAS P. GODICI
Attesting Officer   Acting Director of the United States Patent and Trademark Office